United States Patent [19]
Horstmann et al.

[11] Patent Number: 5,912,008
[45] Date of Patent: Jun. 15, 1999

[54] TRANSDERMAL THERAPEUTIC SYSTEM FOR THE RELEASE OF 17-β-ESTRADIOL AND PROCESS FOR ITS PRODUCTION

[75] Inventors: Michael Horstmann, Neuwied; Sylvia Hahn, Bendorf; Reinhold Meconi; Robert-Pieter Klein, both of Neuwied, all of Germany

[73] Assignee: LTS Lohmann Therapie-Systeme GmbH, Neuwied, Germany

[21] Appl. No.: 08/876,427

[22] Filed: Jun. 16, 1997

Related U.S. Application Data

[63] Continuation of application No. 08/446,755, filed as application No. PCT/EP93/02971, Oct. 27, 1993, abandoned.

[30] Foreign Application Priority Data

Nov. 6, 1992 [DE] Germany ............... 42 37 453

[51] Int. Cl.⁶ .................................................. A61F 13/02
[52] U.S. Cl. ........................................... 424/448; 424/449
[58] Field of Search ..................................... 424/448, 449

[56] References Cited

U.S. PATENT DOCUMENTS

| | | | |
|---|---|---|---|
| 4,668,232 | 5/1987 | Cordes | 604/897 |
| 4,863,738 | 9/1989 | Taskovich | 424/449 |
| 5,393,529 | 2/1995 | Hoffmann | 424/445 |

FOREIGN PATENT DOCUMENTS

| | | |
|---|---|---|
| 0379045 | 7/1990 | European Pat. Off. . |
| 0430491 | 6/1991 | European Pat. Off. . |
| 0483370 | 5/1992 | European Pat. Off. . |
| 2 138 286 | 10/1984 | United Kingdom . |
| 9006736 | 6/1990 | WIPO . |
| 9010425 | 9/1990 | WIPO . |
| 9105529 | 5/1991 | WIPO . |

*Primary Examiner*—D. Gabrielle Brouillette
*Attorney, Agent, or Firm*—Wenderoth, Lind & Ponack, L.L.P.

[57] ABSTRACT

The invention concerns a transdermal therapeutic system comprising the active substance 17-β-estradiol and optionally further active substances, with a laminated structure comprising a backing layer which is substantially impermeable to moisture and impermeable to active substance, one or more matrix layers and, where non-adhesive matrix layers are present, an adhesive layer, characterized in that the concentration of the dissolved estradiol in all matrix layers and, where an adhesive layer is present, in the adhesive layer lies between its saturation concentration in dry condition und its saturation concentration in moist condition, whereby the term "dry condition" is understood to mean that the base material is in equilibrium with a gas phase with less than 10% relative humidity and the term "moist condition" is understood to mean that the base material is in equilibrium with a gas phase with more than 90% relative humidity.

9 Claims, No Drawings

TRANSDERMAL THERAPEUTIC SYSTEM FOR THE RELEASE OF 17-β-ESTRADIOL AND PROCESS FOR ITS PRODUCTION

This application is a continuation of now abandoned application Ser. No. 08/466,755, filed Jul. 10, 1995, which application is a national phase application of International application No. PCT/EP93/02971, filed Oct. 27, 1993.

DESCRIPTION

The invention relates to a transdermal therapeutic system for the release of 17-β-estradiol and optionally further active substances through the skin to the human body.

Transdermal therapeutic systems (TTS) have already been introduced on the market for the pharmaceutic therapy of a series of diseases. Meanwhile, also TTS comprising the active substance 17-β-estradiol have been successful as a therapeutic agent for climacteric complaints, recently also for osteoporosis, commercially as well as in therapy. The systems described in EP 0 421 454 contain estradiol in a water-swellable acrylate polymer with the addition of "crystallization" inhibitors and tackifying resins. However, the influence of varying water vapour tension on the solubility of estradiol was not realized, consequently there is no teaching for the correct adjustment of the concentration of estradiol.

One disadvantage of the systems according to the state of the art is the necessity of employing so-called "enhancers". These are, generally liquid, additives improving the resorption properties of the human skin and thus enabling the absorption of the active substance estradiol from a sufficiently small TTS area. In particular, highly volatile enhancers, such as ethanol, which is frequently used in the case of estradiol, involve problems caused by excessive softening of the adhesive layers of TTS and above all they make further, space-consuming compartments in the system necessary, which render the TTS unacceptably large with respect to its area and/or thick.

When adding certain less volatile enhancers, which are, however, mostly less active, it is possible to manufacture matrix systems containing the active substance and the resorption enhancing components in one or a small number of monolithic layers. U.S. Pat. No. 4,863,738 is one of many examples claiming the application of active substances, e.g. estradiol, together with a particular enhancer (in this case glyceryl mono-oleate) in any desired TTS matrix and in any desired concentration. Unfortunately, according to the state of the art, with such TTS a satisfactory therapy cannot be achieved either, since either the selected enhancers are too poorly tolerated by the skin, or because the systems must have an unacceptably large area owing to the still insufficient flow through the skin. A further problem is presented by the fact that in numerous formulation variants of such systems recrystallization tends to occur for apparently unpredictable reasons so that the systems lose a great part of their therapeutic activity.

Concentration values according to the state of the art can be found, for example, in GB 2 138 286 (between 0.01% estradiol and the saturation solubility in the solvent), in EP 0 421 454 (0.5% to 10% in the polymer) or in BE 899 444 (between 20% and saturation).

It is thus the object of this invention to provide an acceptably thin and, with regard to area, small TTS which contains no readily volatile enhancers, does not suffer from activity losses during storage caused by recrystallization and has nevertheless a high flow rate, relative to area (mg/cm²/h), on the skin.

According to the invention, this object is achieved in a transdermal therapeutic system containing the active substance 17-β-estradiol and optionally further active substances, which has a laminated structure comprising a backing layer substantially impermeable to moisture, one or more matrix layers and optionally an adhesive layer, by employing a concentration of the dissolved estradiol in all matrix layers, and optionally in the adhesive layer, that lies between its saturation concentration in dry condition and its saturation concentration in moist condition, whereby the term "dry condition" is understood to mean that the base material is in equilibrium with a gas phase with less than 10% relative humidity and the term "moist condition" that the base material is in equilibrium with a gas phase with more than 90% relative humidity.

Further valuable characteristics of the transdermal therapeutic system result from its embodiments according to the invention, whereby the system advantageously exhibits an equivalent moisture during manufacture and storage corresponding to a relative humidity of up to 40%. Surprisingly, all matrix layers and, where an adhesive layer is present, the adhesive layer exhibit, in a moisture equilibrium with up to 10% relative humidity, a solubility for the active substance 17-β-estradiol which is at least 50% higher than that in a moisture equilibrium with at least 90% relative air humidity. It is of advantage if all matrix layers and, where an adhesive layer is present, the adhesive layer, consist of an acrylic acid ester copolymer with a solubility for the active substance 17-β-estradiol between 0.2 and 2.0 (g/g), determined in a moisture equilibrium with 10% relative humidity.

Advantageously, one or more of the matrix layers or, where an adhesive layer is present, the adhesive layer, contain one or more substances from the group of tackifiers, skin permeation enhancing additives, filling agents, solubility enhancers or water-swellable additives. In this case, each of the following components may be contained in one or several layers of the matrix and/or in one adhesive layer:

As components of the adhesive resin: tackifying resins such as colophony and the derivatives thereof, polyterpene resins from α- or β-pinene, aliphatic, aromatic or alkylaromatic hydrocarbon resins, melamine-formaldehyde resins, phenol resins, hydroabietyl alcohol and mixtures thereof.

As filling agents: carbonates, phosphates, silicates, sulfates and oxides of the alkaline earth metals, zinc oxide, silicon oxide, cellulose and its derivatives, talcum or titanium dioxide, but also sugars (sugar derivatives) of low solubility such as lactose, or starch derivatives such as cyclodextrine.

As solubility enhancing additives and skin permeation enhancers, respectively: acetylacetone, acetyltributyl citrate, acetyltriethyl citrate, avocado oil, cottonseed oil, benzyl alcohol, butyl stearate, cetyl lactate, cetyl palmitate, cetyl stearate, cetyl stearyl alcohol/cetyl alcohol, chlorobutanol, cineole, decylmethyl sulfoxide, decyl oleate, dibutyl phthalate, diethylene glycol monoethyl ether, diethyl phthalate, diethyl sebacate, diisopropyl adipate, dimethyl phthalate, dimethyl sulfoxide, dioctyl adipate, dipropylene glycol, glyceryl monooleate, glyceryl monostearate, stearyl alcohol, peanut oil, ethyl lactate, ethyl linoleate, ethyl-(9, 12,15)-linolenate, eugenol, farnesol, glycerin, glyceryl acetyl ester, glyceryl stearate, glycol distearate, glyoxal, hexadecanol, hexylene glycol, vaseline, petrolatum, isobutyl stearate, isocetyl stearate, isodecyl oleate, isopropyl lanolate, isopropyl myristate/isopropyl palmitate, isopropyl stearate, isostearyl neopentanoate, lauric acid diethanol amide, limonene, linolenic acid, linoleic acid diethanol amide, almond oil, mint camphor, mint oil, myristyl lactate, myristyl myristate, myristyl stearate, m-tolyl acetate, clove oil, octyl dodecanol, octyl palmitate, octyl stearate, oleic acid diethanol amide, oleyl alcohol, oleyl oleate, olive oil, paraffine, liquid mineral oil, petroleum, peppermint oil, phenylethyl alcohol, isostearic acid, octanoic acid, propylene carbonate, propylene glycol, castor oil/hydrogenated/ refined, safflower oil, squalane, squalene, triacetin, glyceryl triacetate, triethyl citrate, undecylenic acid, propylene glycol, propanediol, 1,3-butylene glycol, (+)-fenchone, ammonium lauryl ether sulfate, cholalic acid, cholesterol, potassium stearate, lecithine, glycerol hydroxy stearate, mono- and diglyceride of nutrient fat acid, sodium caprylate, sodium lauryl ether sulfate, Na-/K-salts of the nutrient fatty acids, Na-lauryl sulfate, PEG-(2)-stearate, sodium sulfosuccinate, polyglyceryl esters of the nutrient fatty acids, polyoxyethylene alkyl ether, cetomacrogol, polyoxyethylene fatty acid sorbitane ester, propylene glycol stearate, sorbitane fatty acid ester, stearic acid diethanolamide.

As water-swellable additives: for example, starch and the derivatives thereof, agar-agar, alginic acid, arabinogalactane, galactomannan, cellulose and its derivatives, carrageen, dextrane, tragacanth and many other rubbers of vegetable origin, as well as water-soluble or water-swellable polymers, such as polyvinyl pyrrolidone, polyvinyl alcohol, polyacrylic acid or polyacrylamide, to mention but a few. Polypeptides such as gelatin, albumin, collagen or egg white.

As crystallization inhibitors phthalic acid ester, adipic ester, mono-, di- and triglycerides, esters of higher-valency fatty acids, long-chain alcohols and the derivatives thereof, derivatives of nonylphenol and octyl phenol, respectively, derivatives of fatty acids, derivatives of sorbite and mannite, non-ionogenic tensides, polyoxyethylene alkyl ether, derivatives of castor oil, sitosterol and polyvinyl pyrrolidone as well as further substances known to the person skilled in the art.

The principle according to the invention, in similar form, also appears in other base materials for transdermal therapeutic systems. In this connection, it is important above all to adjust the estradiol concentration correctly. The concentration of estradiol must be higher than the saturation concentration in moist condition, but lower than the saturation concentration under dry conditions. The manufacture of the systems according to the invention therefore requires experimental solubility determination. Since the water absorption capacity of polymers varies to an extreme degree as well as being dependent on temperature, a description of the conditions "moist" and "dry" by means of absolute concentration values of water in the base material would not describe the conditions with sufficient precision. Rather, it is necessary to use the term of equivalent moisture, commonly used in pharmaceutics. The term is used to describe the moisture picked up by a material which is in equilibrium with a predetermined relative humidity of its environment. Advantageously, determination of the estradiol solubility is carried out in so-called hygrostats, wherein an auxiliary agent of known equivalent moisture (salt solutions, silica gel, phosphorus pentoxide, etc.) is stored, together with the sample, for some time (days up to weeks) in a container which is isolated from the outside. In example 1 attached hereto, practical variants of such hygrostats were used, by means of which equivalent moistures were used corresponding to about 0 up to 1%, but certainly below 10%, relative air humidity—dry condition—(silica gel) and to about 97% up to 98%—moist condition—(so-called physiological saline).

The method to be used for determining the solubility in these experiments is to be adapted to the respective problem by the person skilled in the art. Example 1 describes a simple method therefor. In this example, sample formulations with varying active substance loads were prepared and stored under humidity-controlled conditions. Subsequently, it is determined merely visually, or microscopically whether the active substance is now present either completely dissolved or in precipitated form.

The equivalent moisture corresponding to a relative air humidity of below 40%, which is advantageous for the production and storage processes, can also be achieved, apart from employing the hygrostat principle, by adequate protection (packaging) of the material from the ambient air. A process for the production of TTS according to the invention is provided according to the features described herein.

Thus, the invention provides a process for the production of a transdermal therapeutic system, characterized in that at room temperature the active substance is stirred together with components of the matrix layer or adhesive layer, respectively, as well as with one or more additives from the group of tackifiers, skin permeation-enhancing additives, filling agents, solubility enhancers and/or water-swellable additives until a homogeneous suspension is obtained and are subsequently coated onto a sheet which has been rendered dehesive, such that a comparatively thin layer thickness results, subsequent to which the coating is dried at stepwise increased temperatures for some minutes at each temperature, ultimately at 120° C., and a covering sheet is immediately applied onto the dried layer, such that no air bubbles occur, employing roll pressure, and said layer is laminated therewith covering the same, whereafter, finally, individual transdermal systems of defined area are punched out. More particularly, the process is characterized in that the coating of the sheet, which sheet has been rendered dehesive, is applied with a coating mass of 100 g/m$^2$, relative to the solvent-free portion. More specifically, the process is characterized in that drying of the layer is carried out at 40° C., 60° C., 80° C. and 120° C., for 4 minutes at each temperature.

EXAMPLE 1

To determine how the solubility of 17-β-estradiol is influenced by varying storage humidity, first the following active substance-containing adhesive layers were used (layer thickness in all cases ca. 60 micrometers):

A: acrylate polymer with 0.3% estradiol

B: acrylate polymer with 0.45% estradiol

C: acrylate polymer with 0.6 estradiol

D: acrylate polymer with 0.8 estradiol

E: acrylate polymer with 1.0% estradiol

F: acrylate polymer with 1.3% estradiol

G: acrylate polymer with 2.0% estradiol

H: acrylate polymer with 3.0% estradiol

To protect the surfaces, the layers were laminated between a 15-micrometer-thick PETP membrane and an object slide of glass (76×26 mm) in such a manner that air bubbles were prevented.

The samples were sealed together with the required humidity controlling device (see below) in a sealable composite packing material (paper/aluminium/ethylene-vinyl acetate) and stored at room temperature for one year.

Humidity controllers:

1. "Moist": inserted strip of nonwoven, saturated with ca. 1 ml 0.9% sodium chloride solution in water 2. "Dry": ca. 10 grains of blue gel, about 1 g As each sample A-H was stored under both conditions, 16 different observation patterns resulted:

After expiry of the storage time, the samples were examined for precipitations of the active substance. Only crystals which were present distributed over a certain area and were microscopically clearly recognizable were rated as "recrystallization".

| Active substance content | Result "dry" | Result "moist" |
| --- | --- | --- |
| 0.3% estradiol | completely dissolved | completely dissolved |
| 0.45% estradiol | completely dissolved | completely dissolved |
| 0.6% estradiol | completely dissolved | precipitation |
| 0.8% estradiol | completely dissolved | precipitation |
| 1.0% estradiol | completely dissolved | precipitation |
| 1.3% estradiol | completely dissolved | precipitation |
| 2.0% estradiol | precipitation | precipitation |
| 3.0% estradiol | precipitation | precipitation |

Consequently, the concentration range in which the principle according to the invention can be used lies between 0.6 and 1.3% estradiol (g/g).

EXAMPLE 2

Preparation of a system according to the invention

| | |
| --- | --- |
| 1.0 g | 17-β-estradiol |
| 60.0 g | Cariflex ® 1107 (styrene-isoprene-styrene block-copolymer) |
| 138.0 g | Foral ® 85 (thermoplastic ester resin of colophony derivatives) |
| 200.0 g | petrol (boiling range 80 to 100° C.) | are stirred in a cylindrical glass vessel at room temperature until a homogeneous suspension is obtained, and thereafter coated, employing a continuously operating coating machine, on a siliconized polyester film having a thickness of 100 g/m² (relative to the solvent-free portion) results. The coating is dried at 40° C., 60° C., 80° C. and at 120° C., each time for 4 minutes. Immediately thereafter, a 15-micrometer-thick polyester film is applied to (laminated on) the dried layer, employing roll pressure.

By punching with a wad punch, transdermal systems of 16 cm² are obtained.

By employing the transdermal therapy system, the following advantageous effects are achieved:
good resorption properties of the human skin
good skin tolerance
sufficient active substance flow through the skin combined with an acceptably large TTS area
no recrystallization of the active substance during storage.

We claim:

1. In a transdermal therapeutic system containing the active substance 17-β-estradiol and optionally further active substances, having a laminated structure comprising a backing layer which is substantially impermeable to moisture and impermeable to active substance, one or more layers of matrix containing as essential ingredients a polymer acting as a solvent for 17-β-estradiol, a tackifier, a solubility enhancing additive and a skin permeation enhancer and, where non-adhesive matrix layers are present, an adhesive layer, the improvement wherein the concentration of 17-β-estradiol dissolved in all matrix layers and, where an adhesive layer is present, in the adhesive layer, is lower than its saturation concentration under dry condition and higher than its saturation concentration under moist condition said concentration being 0.6 to 1.3% (g/g), wherein the term "dry condition" means matrix material in equilibrium with a gas phase with less than 10% relative humidity, and the term "moist condition" means matrix material in equilibrium with a gas phase with more than 90% relative humidity.

2. A transdermal therapeutic system according to claim 1 wherein during manufacture and storage the system has an equivalent moisture corresponding to up to 40% relative humidity.

3. A transdermal therapeutic system according to claim 1, wherein all matrix layers and, where an adhesive layer is present, the adhesive layer, in a moisture equilibrium with up to 10% relative humidity, have a solubility for the active substance 17-β-estradiol which is at least 50% higher than that in a moisture equilibrium with at least 90% relative humidity.

4. A transdermal therapeutic system according to claim 3, wherein all matrix layers and, where an adhesive layer is present, the adhesive layer, consist of an acrylic acid ester copolymer having a solubility for the active substance 17-β-estradiol of between 0.2 and 2.0% (g/g), determined in a moisture equilibrium with 10% relative humidity.

5. In a process for the manufacture of a transdermal therapeutic system containing the active substance 17-β-estradiol and optionally further active substances, having a laminated structure comprising a backing layer which is substantially impermeable to moisture and impermeable to active substance, one or more matrix layers and, where non-adhesive matrix layers are present, an adhesive layer, the improvement wherein the concentration of 17-β-estradiol dissolved in all matrix layers and, where an adhesive layer is present, in the adhesive layer, is selected to be lower than its saturation concentration under dry condition and higher than its saturation concentration under moist condition, wherein the term "dry condition" means matrix material in equilibrium with a gas phase with less than 10% relative humidity, and the term "moist condition" means matrix material in equilibrium with a gas phase with more than 90% relative humidity and wherein during manufacture and storage the system is maintained under conditions such that it has an equivalent moisture corresponding to no more than 40% relative humidity to prevent activity loss by recrystallization of the 17-β-estradiol during storage.

6. A process according to claim 5, which comprises stirring together, at room temperature, the active substance with components of the matrix layer or adhesive layer, respectively, and with one or more additives from the group consisting of tackifiers, skin permeation-enhancing additives, filling agents, solubility enhancers and water-swellable additives until a homogeneous suspension is obtained, subsequently coating the mixture onto a sheet which has been rendered dehesive, in a manner such that a comparatively thin layer thickness results, subsequently drying the coating at step-wise increased temperatures for some minutes at each temperature, ultimately at 120° C., and immediately applying a covering sheet onto the dried layer, in a manner such that no air bubbles occur, employing roll pressure, and laminating said layer therewith to cover the same, and subsequently punching out individual transdermal systems of a defined area.

7. A process according to claim 6, wherein the coating of the sheet, which sheet has been rendered dehesive, is applied with a coating mass of 10 g/m², relative to the solvent-free portion.

8. A process according to claim 6, wherein stepwise drying of the layer is carried out at 40° C., 60° C., 80° C. and 120° C., for 4 minutes at each temperature.

9. A transdermal therapeutic system according to claim 1, which further contains filling agents, water-swellable additives, or both.

* * * * *